(12) United States Patent
Sheldrick

(10) Patent No.: US 11,565,289 B1
(45) Date of Patent: Jan. 31, 2023

(54) MULTI-CHAMBER MEDICAL WASTE OZONE-BASED TREATMENT SYSTEMS AND METHODS

(71) Applicant: Ralph Sheldrick, Winchester (CA)

(72) Inventor: Ralph Sheldrick, Winchester (CA)

(73) Assignee: Viking Ozone Technology, LLC, Houston, TX (US)

( * ) Notice: Subject to any disclaimer, the term of this patent is extended or adjusted under 35 U.S.C. 154(b) by 0 days.

(21) Appl. No.: 17/576,801

(22) Filed: Jan. 14, 2022

(51) Int. Cl.
*B09B 3/00* (2022.01)
*B09B 3/70* (2022.01)
*A62D 3/38* (2007.01)
*B09B 3/35* (2022.01)
*A61L 2/20* (2006.01)
*B09B 3/38* (2022.01)
*B09B 101/65* (2022.01)

(52) U.S. Cl.
CPC ............... *B09B 3/70* (2022.01); *A61L 2/202* (2013.01); *A62D 3/38* (2013.01); *B09B 3/35* (2022.01); *B09B 3/38* (2022.01); *A61L 2202/122* (2013.01); *A61L 2202/15* (2013.01); *B09B 2101/65* (2022.01)

(58) Field of Classification Search
CPC ........................................................ B09B 3/00
USPC ............................................................ 422/28
See application file for complete search history.

(56) References Cited

U.S. PATENT DOCUMENTS

2009/0004051 A1 * 1/2009 Firestone .............. B09B 3/0075
422/1

* cited by examiner

*Primary Examiner* — Gregory E Webb
(74) *Attorney, Agent, or Firm* — Wilkinson Law Office; Clinton H. Wilkinson

(57) ABSTRACT

Ozone-based methods and systems for treatment of solid waste that contains pathogens, and requires apparent volume reduction, include using dual treatment chambers, lift transporters that cascade the preliminarily treated solid waste, and agitation within the second (high ozone concentration) treatment chamber. The steps include feeding solid waste into a shredder chamber to reduce its apparent volume; and then to a first treatment chamber for preliminary ozone molecular interaction with the solid waste, and to a second treatment chamber with an agitator, via at least one lift transporter, to both cascade and agitate to enhance efficacy.

23 Claims, 13 Drawing Sheets

Figure 7 Collection Chamber Side View

MULTI-CHAMBER MEDICAL WASTE OZONE-BASED TREATMENT SYSTEMS AND METHODS

BACKGROUND OF INVENTION a. Field of Invention

This invention relates to treatment of solid waste materials that contain viruses and/or other pathogens, and require volumetric reduction, and particularly systems and methods for treating medical waste. The purposes include controlled reduction/elimination of the pathogens, and subsequent reduction of potential infectious diseases; and the shredding of the waste to reduce sharp objects and reduce volumetric needs; and to render the treated waste acceptable for general and common waste handling, such as landfill. These purposes are particularly essential for clinics, hospitals, medical centers, doctor offices, health care and senior care facilities, and medical test centers. This invention is particularly directed to the aforesaid systems and methods utilizing ozone to destroy the pathogens, including prion diseases (transmissible spongiform encephalopathies), at a molecular level. The term "medical waste" as used herein should be interpreted broadly to include waste that contains one or more dangerous or potentially dangerous organisms or micro-organisms, including viruses and other pathogens. Thus, the term includes such waste as is generated by medical facilities and medical treatment, research and test centers, including hospitals, clinics, laboratories, blood banks, mortuaries, doctors' and dentists' offices, pharmacies, home based and healthcare retirement homes and assisted facilities, veterinary clinics, tattoo parlors and vaccination facilities and clinics. It also includes less traditional waste with dangerous or potentially dangerous organisms or micro-organisms, such as solid waste with micro-organisms that eat polymers and defecate monomers, solid waste with organisms developed for military bio-warfare, solid waste from bio-mutation experiments for whatever purpose, solid waste with bio-bugs that consume petro spills, solid waste from concentrated health threats, such as jails, prisons, rehab centers, cruise ships and airports, etc. "Apparent volume" as used herein means the space occupied by the solid waste and any airspace therebetween, such as the volume of a full solid waste bin before treatment, as well as the subsequent reduced volume after shredding. The term "pathogen" as used herein should likewise be broadly construed to mean any agent that may cause infection, disease or illness.

b. Description of Related Art

The following patents are representative of the field pertaining to the present invention:

U.S. Pat. No. 10,946,422 B2 to Jude et al describes a method and system for treating biomedical waste on site, that includes, among other features, a shredder, an upwardly inclined auger chamber, and a waste receptacle. The shredder shreds unsterilized waste and feeds into the lower end of the inclined auger chamber. The chamber includes ozone injectors to treat waste as the auger conveys it upward toward an outlet that drops the sterilized waste into the waste receptacle. The incline of the chamber allows for a smaller system footprint with sufficient processing capacity to satisfy the needs of smaller hospitals and clinics. Unlike the present invention, this prior art system utilizes its auger as its primary zone treatment component and, contrary to the present invention transporters that cascade the solid waste into a primary treatment chamber of ozone, this Jude et al system shows a "plug" of treated waste at the top of its auger to minimize escape of ozone. This process is virtually identical to the methods used in microwave waste treatment technology. The use of a Humidizone is not mentioned here and claims of 100% solubility of ozone in water from this process are unfounded. As with other processes, the "plug" reduces porosity through compaction and compression of the waste, limiting the exposure and effects of ozone on the waste. Both limited flow auger systems and hydraulic transport of the waste before or during processing reduces porosity of the waste and thereby reduces the exposure to ozone for the destruction of virus and pathogens.

U.S. Pat. No. 9,199,242 B2 to Barberi et al describes a system for hazardous waste sanitation and removal devices, along with methods of sanitizing hazardous waste materials, that include: a) a unitary shredder system, b) a transport system, a pre-treatment system or a combination thereof, comprising a reciprocating operation system, c) a treatment system, d) a dewatering system, a desolutionizing system or a combination thereof, and e) a collection system for disposal. Dewatering processes are also disclosed that includes at least one collection of wastes, at least one screw press, at least one conveyor system that carries the at least one collection of wastes after interaction with the at least one screw press, and at least one filter system. The Barberi systems require plumbing and water treatment along with a physical press component.

U.S. Pat. No. 8,784,746 B2 to Jude et al describes a method and system to improve throughput of biomedical waste treatment. Their ozone-based system includes a shredder, a roll-off treatment bin with ozone injectors, an ozone source, and a controller. The controller monitors electric current drawn by the shredder as shredded waste enters the ozone-enriched treatment bin. In response to current falling below a predetermined low level, indicating that a batch of waste has been shredded and loaded into the treatment bin, the controller starts a treatment timer. The timer measures elapsed ozone treatment or exposure time. If additional waste is added to the shredder and a subsequent low-current condition is detected, the controller restarts the treatment timer. Expiration of the timer indicates that the waste in the roll-off bin is sterilized and ready for transport to landfills. There is also an elastic seal assembly described.

U.S. Pat. No. 8,652,405 B2 to Jude et al like the previous prior art patent, describes a method and system to improve throughput of biomedical waste treatment. This ozone-based system includes a shredder, a roll-off treatment bin with ozone injectors, an ozone source, and a controller. The controller monitors electric current drawn by the shredder as shredded waste enters the ozone-enriched treatment bin. In response to current falling below a predetermined low level, indicating that a batch of waste has been shredded and loaded into the treatment bin, the controller starts a treatment timer. The timer measures elapsed ozone treatment or exposure time. If additional waste is added to the shredder and a subsequent low-current condition is detected, the controller restarts the treatment timer. Expiration of the timer indicates that the waste in the roll-off bin is sterilized and ready for transport to landfills. There is also a restart feature that responds to a change in operational status of the shredder.

U.S. Pat. No. 8,518,339 B1 to Jude et al, like the prior two patents above, describes a method and system to improve throughput of biomedical waste treatment, the present inventors devised an exemplary ozone-based system including a shredder, a roll-off treatment bin with ozone injectors, an ozone source, and a controller. There is also a lateral conveyor included. The controller monitors electric current drawn by the shredder as shredded waste enters the ozone-enriched treatment bin. In response to current falling below a predetermined low level, indicating that a batch of waste has been shredded and loaded into the treatment bin, the controller starts a treatment timer. The timer measures elapsed ozone treatment or exposure time. If additional waste is added to the shredder and a subsequent low-current condition is detected, the controller restarts the treatment timer. Expiration of the timer indicates that the waste in the roll-off bin is sterilized and ready for transport to landfills.

U.S. Pat. No. 8,425,857 B2 to Glazer et al describes a method and a system for ozone sterilization of waste material that includes a tank configured to receive waste material, ozonated water, and ozone gas. The system further includes a pump coupled to the tank to receive the waste material and the ozonated water from the tank and form a slurry. The pump includes a cutter assembly to reduce a particle size of the slurry through cutting. Additionally, the system includes a circulation loop coupled between the tank and the pump to receive the slurry from the pump and re-circulate the slurry to the tank until the slurry is sterilized.

U.S. Pat. No. 7,550,111 B2 to Jude et al describes an apparatus for processing biomedical waste that includes a waste input container having an input door in a top thereof and an output door in a bottom thereof. A shredder is mounted under the output opening and is operative to shred waste to a desired maximum size. A processing chamber is located under the shredder such that, when the output door is open, solid waste deposited in the waste input container passes through the output opening and through the shredder, and shredded waste drops into the processing chamber. Ozone gas is directed into the processing chamber, and an ozone indicator indicates ozone concentration. Exhausts are selectively operative to exhaust the atmosphere from the processing chamber and waste input container.

Notwithstanding the prior art, the present invention is neither taught nor rendered obvious thereby. Among the present invention unique features, components and steps, are the cascading of treated solid waste after shredding to create and maintain a high level of porosity throughout the entire waste volume, initial ozone treatment, the tilted waste transporter that is open ended at its lower input end and at its upper output end, and the agitation of solid waste in the primary treatment chamber.

SUMMARY OF INVENTION

The present invention relates to the treatment of solid waste materials that contain viruses and/or other pathogens, and that require volumetric reduction, and particularly systems and methods for treating medical waste, involving unique steps and components that increase the efficiency and efficacy of the treatment of medical and other solid waste. There are four stages involved in the preferred embodiments of the processing technology, systems and methods of the present invention: Stage One: the pre-shredding waste handling assembly complete with shroud, air curtains, UV lighting, exhaust fan, particle filters, HEPA filters, Carulite ozone destruction, activated charcoal bed for odor control, exhaust conduit and waste transport conveyor. Stage two: the shredding assembly including the shredded waste collection structure for initial treatment (first treatment chamber), the inclined waste transport hardware and ozone injection and ozone sampling piping network. Stage three: the primary treatment chamber with cascading and with agitation assembly, unload transport system, ozone injection, ozone destruct system, one-way air inlet valves, pressure equalization system, ozone destruct assembly using Carulite catalyst or other catalyst, ozone monitoring system to control ppm level during treatment, stainless steel components and construction, seals of Viton or equivalent to contain ozone and safety controls to protect the operators and environment. Stage four: the ozone destruct chamber for decanting any excess residual ozone that is not consumed by the processing of bio-hazardous waste in the primary treatment chamber. The ozone destruct chamber has an ozone destruct assembly utilizing Carulite or other catalyst, exhaust fan to create a negative pressure in the chamber during decanting, one-way air valves to allow air flow into the chamber during decanting, ozone monitoring components to measure the ppm level of the decanting chamber, unloading transport assembly to evacuate the waste once a zero ppm level of ozone is reached and maintained, an agitation assembly is utilized to tumble the treated waste thereby maintaining a high level of porosity allowing any trapped ozone in the treated waste to dissipate and be converted back to oxygen and exhausted from the chamber.

Thus, the present invention systems and methods are ozone-based methods for treatment of solid waste that contains at least one pathogen, and requires apparent volume reduction, which include using multiple treatment chambers, the first being a low ozone concentration collection chamber, and the second being a high ozone concentration treatment chamber, and a final unit for decanting, which is preferably a separate final decanting chamber. Additional advantageous and efficiency enhancing feature include lift transporters that cascade the preliminarily treated solid waste, and agitation within the second (high ozone concentration) treatment chamber. The steps include feeding solid waste that contains at least one pathogen from a source into a shredder chamber that has at least one a shredder and shredding the solid waste to reduce its apparent volume; feeding the solid waste from the shredder chamber to a first treatment chamber having an ozone source connected thereto, being an initial treatment chamber, for preliminary ozone molecular interaction with the solid waste, to destroy at least a portion of the pathogens; feeding the preliminarily treated solid waste from the first treatment chamber to a second treatment chamber having an ozone source connected thereto, via at least one lift transporter. The lift transporter is tilted upwardly and has an open, lower inlet end and an open, upper outlet end, so that when it transports the preliminarily treated solid waste upwardly into the second treatment chamber, it spreads the solid waste particles in a scattered manner into a cascade of solid waste that, via gravity, falls into the high concentration ozone, so as to increase surface area exposure of the solid waste to the ozone, and to increase efficacy of ozone treatment. This exemplary cascading process creates and maintains a high level of porosity of the waste throughout the treatment process increasing the exposure of the shredded waste to ozone in the collection chamber and the treatment chamber and subsequently the decanting chamber. Additionally, and significantly, the second treatment chamber, being a primary treatment chamber, includes at least one rotating agitator to stir up and agitate the solid waste that has been cascaded, for further scattering of the solid waste to again further increase surface area exposure of the solid waste to the ozone treatment, and to further increase efficacy of ozone treatment. Additional steps include eliminating remaining ozone from the solid waste; and discharging the shredded, treated apparent volume-reduced solid waste with an exit transport mechanism into a transport device for disposal or subsequent use, such as a fuel.

In some embodiments of the present invention there is a single lift transporter while in others there is a plurality of lift transporters. The lift transporter(s) are selected from the group consisting of: a positive pressure transporter, a negative pressure transporter, a conveyor transporter, and an auger transporter. In some preferred embodiments, the lift transporter is one or more open ended auger(s).

The agitator(s) located within the second treatment chamber are preferably tumbler type agitators, i.e., rotating fins. Alternatively, they may be paddles such as rotating on a central axis, e.g., a horizontal axis, rotating spiral fins, rotating drum, and rotating drum with fins, or combination thereof.

In the present invention systems and methods, the unspent ozone is eliminated in an ozone destruction device that may be functionally connected downstream from the second treatment chamber to prevent ozone release to the atmosphere or may be positioned in an exhaust above said second treatment chamber. Alternatively, there is a decanting chamber functionally connected to the second treatment chamber and positioned between the second treatment chamber and an exit transport mechanism, and the ozone destruction device is connected to said decanting chamber. The decanting chamber preferably includes at least one rotating agitator to assist in the separation of unspent ozone from the treated solid waste.

In present invention preferred embodiments, the ozone source connected to the first treatment chamber is adapted to provide ozone at 50 to 500 ppm and the ozone source connected to the second treatment chamber is adapted to provide a higher ozone concentration, at 5000 to 7000 ppm. Also, in some preferred embodiments, the systems and methods include treating the incoming solid waste with ultraviolet light prior to or upon entering the shredder chamber before shredding.

The ozone-based method for treatment of solid waste in the present invention is a continuous process. This means that the system does not start and stop or respond to conductivity or other stop and go signals, but rather runs continuously during the entire feed and treat process.

The primary treatment chamber is fitted with pressure equalization lines to eliminate the potential for pressure build-up of the ozone inside the treatment chamber resulting in a positive pressure which would adversely affect the injection of ozone gas into the space and placing stress on seals and the physical structure of the holding vessel. The treatment chamber is also fitted with one-way air inlet valves to allow outside air to enter the chamber during the decanting of the ozone process and reducing the ppm level to zero prior to final unloading of the treated waste for disposal. The one-way valves improve the decanting process in both time and effectiveness without creating a negative pressure in the vessel effecting the physical structure of the vessel including seals and other components used to control and maintain the containment of the ozone gas during processing.

The system is not designed for hazardous waste material including non-shreddable material like titanium joints, explosive or flammable materials, batteries, charcoal filters, corrosive agents including acids and large volumes of liquids. Typical medical waste has a 20% volume of moisture by weight. Some of the moisture within the waste materials, while in the presence of a high concentration and atmospheric volume of ozone will convert to a hydroxyl radical which has a powerful oxidizing ability and useful in destroying red blood cell among other benefits. High grade ozone produced from oxygen has the ability to breakdown double carbon bond (C=C) and this type of carbon-to-carbon bond is found in many biological molecules, and in other types of organic compounds, most notably pharmaceuticals. Ozone is extremely effective to promote the degradation/destruction of a large number of drug compounds, as well as other pathogens. The critical parameter for ozone is not time, as in steam or ethylene oxide sterilization processes; it is the ozone concentration (dose) injected into the chamber.

Additional features, advantages, and embodiments of the invention may be set forth or apparent from consideration of the following detailed description, drawings, and claims. Moreover, it is to be understood that both the foregoing summary of the invention and the following detailed description are exemplary and are intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

12 shows a front view thereof.

DETAILED DESCRIPTION OF THE EMBODIMENTS

Figure 1:
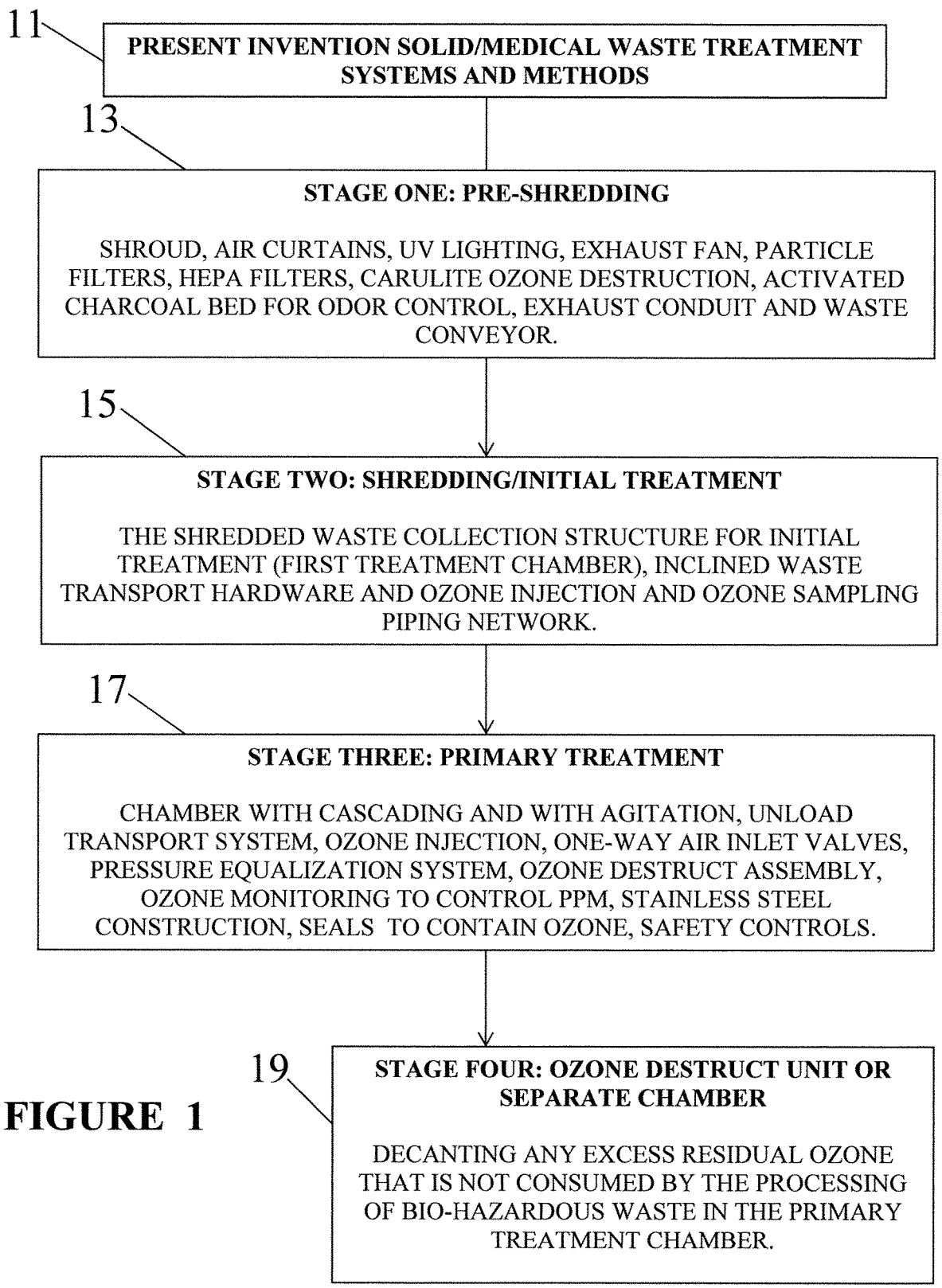
FIG. 1 is a block diagram showing the four general stages of the present invention methods and systems for treating medical waste and other solid waste materials.

The present invention methods and systems (connected diverse devices) are environmentally friendly that are directed to eliminating health risks from medical and other dangerous solid wastes, and also converting that waste into land-fill friendly product or biofuel energy generators using ozone in a very effective way. Ozone ($O^3$) kills all known viruses and pathogens—including destroying prion diseases. Waste is sterilized at a molecular level with ozone. Ozone has broad-based use for destroying pathogens, including in air filtration, as well as solids treatment and especially medical waste treatment. Our advanced ozone technology is designed and built for the processing of RMW (Regulated Medical Waste) and similar solid waste materials. Ozone is produced from compressed ambient air and is filtered to remove water and oils and supplied to PSA (pressure swing absorption fractionators) or VSA (vacuum swing absorption fractionators), or equivalent, to produce 95+(ninety-five plus) percent oxygen ($O^2$) and discharged into corona or plasma block or equivalent ozone generators to create high quality ozone ($O^3$) for the process.

Medical waste is received from hospitals or medical clinics (as well as from prisons, military bases, mortuaries, biotech laboratories, blood banks, veterinary hospitals, dental offices and crime scene cleanups, among others) in bulk and is typically packaged in sealed cardboard boxes or plastic red bags, for regulated medical waste. These boxes or bags can be barcoded to designate their source and contents. The waste, once delivered to the waste processing facility, is weighed and recorded via barcode and moved to the start of the waste treatment system to be loaded and processed.

For a system built with a conveyor configuration, the waste is placed manually or otherwise dumped onto the conveyor belt. The belt moves the waste towards the processing unit and into a covered shroud that has air curtains at the entry and additional air curtains internally. The air curtains preform multiple functions a) to limit the amount of air entering the conveyor shroud and b) stopping any particulates from exiting the conveyor assembly. The horizontal feed-in conveyor is operated by an optic (or equivalent switching mechanism) control to stop and start the conveyor to avoid overloading the shredder hydraulic feed mechanism. In the methods and systems of the present invention, these details are viable options, such as air curtains to assist in ozone isolation/containment, although other known isolation techniques/equipment could be used. For continuous processes of the present invention, in some embodiments, air curtains are preferred.

In some embodiments of the present invention, when a conveyor is used for feeding, the conveyor shroud assembly has a negative air pressure resulting from the exhaust fan located above the shredder receiving floor or pocket, located in the shredder chamber. The floor is the lower portion of the shredder hydraulic ram assembly that forces the raw waste in bag or boxes onto the rotating shredder shaft. The waste is exposed to UV (ultraviolet) light as it moves along the conveyor to the shredder. The multiple UV lights of selected wave lengths are positioned inside the conveyor shroud to reduce any possible exposure to the operators (either direct or reflected). The UV lights form part of the front/receiving assembly self-cleaning feature and work in conjunction with a low level of ozone injected into this space. Thus, in the present invention, both the ultraviolet lights and some ozone injection acts to pretreat the waste and to sanitize the conveyor. The UV lights and low-level ozone ensure that any living virus or pathogens that may be present on the boxes or bags of raw waste or that have contacted the conveyor, are deactivated and can no longer cause illness, infection, or replicate.

In some other embodiments of the present invention, a feed conveyor is not used. For a present invention system built with a cart lifting mechanism, UV (ultraviolet) lights are installed in the receiving hopper shroud and fitted with air curtains to limit air inflow and eliminate any particulates or splatter from exiting the receiving hopper during the dumping/filling process.

In the present invention system, the ozone level in the conveyor or in the cart lift/receiving hopper shroud area can be raised or lower to zero depending on the type of waste being processed. The UV light can be operated manually or automatically through the computer-operating HMI (Human Machine Interface) control center. Also, for safety, the shroud area must be sterilized by ozone and UV light prior to opening for service to safeguard the operators and service staff. Procedures for this function are provided by the trainers during commissioning.

Once the untreated solid waste has entered the shrouded area by conveyor or lifting mechanism, it drops down by gravity into the shredder chamber, onto the shredder floor or pocket. The shredder chamber has an internal hydraulic pump and cylinder to force the waste onto the rotating shredder shaft. The operation of the shaft (rotation) is from the top down cutting the boxes and bags into strips and then forces them onto the cutter anvil to be custom sized before processing. The sizing screen allows waste particles to pass through the screen opening if they are less than the screen opening dimensions. Larger particles are transported around the rotating shaft and forced onto the cutter anvil to be further reduced in size. This process will continue and repeated until all the waste is adequately reduced in sized to easily pass through the sizing screen.

Typically, the sizing screen is 1.5 inches (3.8 cm) to expose the waste to the ozone with the highest level of porosity. In many locations, the shredded waste must not be recognizable as medical waste, once it is shredded. The 1.5-inch screen size will achieve this requirement, although smaller screen sizes can be used, depending upon the intended destiny of the finished waste. The extent of shredding and screen size dictate the apparent volume reduction achieved.

High grade ozone is injected into the shredder screen area and is metered in liters per minute to achieve a level of approximately 30 to 50 PPM (parts per million). The shredder screen area has an ozone sampling orifice and stainless-steel pipe connection to an ozone monitor (such as a Teledyne 465 M or equivalent device) to measure the level of ozone present in this location. The ozone monitor can measure the ozone level in the collection (first) treatment chamber and the shredder screen area alternatively by switching a divertor valve on the sampling piping network. Alternatively, individual monitors may be dedicated to specific locations.

The preferred ozone level in the shredder chamber is approximately 50 PPM and the ozone can migrate up into the receiving hopper shroud area or the conveyor shroud area respectively by the windage of the rotating shaft of the shredder. (1 mg/L=approximately 1 PPM).

TABLE 1

Typical Dosage of Ozone and Reaction Times for Selected Pathogens

*Aspergillus Niger* (black Mount): Destroyed by 1.5 to 2 mg/l.
*Bacillus* Bacteria: Destroyed by 0.2 mg/l within 30 seconds
*Bacillus Anthracis*: Causes anthrax in sheep, cattle and pigs. A human pathogen. Ozone susceptible.
*Clostridium* Bacteria: Ozone-Susceptible.
*Clostridium Botulinum* Spores: Its toxin paralyzes the central nervous system, being a poison multiplying in food and meals. 0.4 to 0.5 mg/l.
Diphtheria Pathogen: Destroyed by 1.5 to 2 mg/l.
Eberth Bacillus (Typhus abdominalis): Destroyed by 1.5 to 2 mg/l.
Echo Virus 29: This virus most sensitive to ozone. After a contact time of 1 Minute at 1 mg/l of ozone, 99.999% killed.
Escheriachia Coli Bacteria (from feces): Destroyed by 0.2 mg/l within 30 seconds.
Encephalomyocarditis Virus: Destroyed to zero level in less than 30 seconds with 0.1 to 0.8 mg/l.
Enterovirus Virus: Destroyed to zero level in less than 30 seconds with 0.1 to 0.8 mg/l
GDVII Virus: Destroyed to zero level in less than 30 seconds with 0.1 to 0.8 mg/l.
Herpes Virus: Destroyed to zero level in less than 30 seconds with 0.1 to 0.8 mg/l.
Influenza Virus: 0.4 to 0.5 mg/l.
Klebs-Loffler Virus: Destroyed by 1.5 to 2 mg/l.
Poliomyelitis Virus: Kill of 99.999% with 0.3 to 0.4 mg/l in 3 to 4 minutes.
Proteus Bacteria: Very Susceptible.
Pseudomonal Bacteria: Very Susceptible.
Rhabdovirus Virus: Destroyed to zero level in less than 30 seconds.
*Salmonella* Bacteria: Very Susceptible.
Staphylococci: Destroyed by 1.5 to 2 mg/l.
Stomatitis Virus: Destroyed to zero level in less than 30 seconds with 0.1 to 0.8 mg/l.
*Streptococcus* Bacteria: Destroyed by 0.2 mg/l within 30 seconds An environment of 50 PPM at the shredder far exceeds the minimum requirement for the dangerous pathogens to be destroyed. Below the shredder screen is a first treatment chamber that operates with a low volume ozone, but greater than at the shredder.

The conveyor shroud or the receiving hopper shroud (lifting mechanism) is fitted with an exhaust fan to create the negative pressure requirement for the loading area of the system. The exhaust fan may be designed and built with a replaceable (and washable) stainless steel particle filter positioned before a Curulite 200 or equivalent ozone destruct chamber and a HEPA filter (replaceable) located before the fan. The shroud area exhaust is preferably plumbed to the exterior of the facility through a roof or wall. The ozone destruct unit using Carulite 200 catalyst is designed and built to be replaceable with new catalyst material. To ensure proper ozone destruction, the unit should be supplied (replaced) with new Carulite every two years or less depending on the number of hours of processing. The exhaust gas is now simply oxygen without VOCs of other dangerous compounds. The waste is treated at room temperature without heat, steam or dangerous chemical resulting in zero emissions. This exemplary process also eliminates the potential for offensive odors being created and emitted/exhausted from the system.

At this point of the process, the waste has had its first exposure to the ozone agent in the shredder chamber and screen location. As mentioned, there is a first (collection) treatment chamber below the screen and this treatment chamber has least one ozone source connected to it for preliminary ozone molecular interaction with the solid waste to destroy at least a portion of pathogen(s). In this initial (first) treatment chamber that is dedicated to destruction of pathogens, the ozone density is increased to be in a preferred range of 50 to 500 ppm.

The shredded and partially treated solid waste is next moved from the first treatment chamber, i.e., the collection treatment chamber, to a primary (second) treatment chamber via at least one lift transporter, tilted (inclined) upwardly to have an open, lower end and an open, upper end, the upper end, wherein the lower end is functionally connected to the first treatment chamber to receive and move the solid waste from the first treatment chamber into the second treatment chamber at an elevated level, and to cascade the solid waste out of the lift transporter upper end and into the second chamber in a scattered manner to increase surface area exposure of the solid waste to the ozone to increase efficacy of ozone treatment. Additionally, the lift transporter open upper end is positioned to also feed the solid waste via cascading into at least one agitator for further scattering of the solid waste to further increase surface area exposure of the solid waste, enhancing its porosity to the ozone to further increase efficacy of ozone treatment. Thus, the present invention systems and methods have dual treatment chambers with "triple action" treatment: a first treatment in the shredder chamber and first treatment chamber, a second treatment during the cascading of the solid waste in the second treatment chamber, and a third treatment through the tumbling agitation in the second treatment chamber. The lift transporter may be one or more transporters and they are selected from the group consisting of a positive pressure transporter, a negative pressure transporter, a conveyor transporter, and an auger transporter, although auger transporters are preferred due to their dual function of lifting and mixing.

In a preferred embodiment, the solid waste is transported by an inclined multiple auger assembly-type transporter lower end below the shredder screen and upper end extending into the primary (second) treatment chamber. The speed and size of the augers do not cause compaction of the waste during the transport from the first treatment chamber to the second treatment chamber but freely disperse the delivered waste in a cascading fashion into the high ozone treatment chamber. A quantity of ozone from the shredder screen area and first treatment chamber is transposed along with the waste to the primary treatment chamber. The waste cascades from the inclined transport auger attached to the primary treatment bin and flows by gravity to the bottom of the chamber, e.g., a stainless-steel bin. The primary treatment chamber has been charged with ozone prior to receiving any shredded waste. Ozone is 1.66 times heavier than air and will collect at the lowest point of the treatment chamber at a higher concentration than the highest point where the ozone sampling takes place. Agitation of the waste, in addition to maintaining a high level of porosity of the waste, disperses the ozone concentration evenly though out the treatment chamber increasing the efficiency and effectiveness of the process.

The charge level of ozone is approximately 5000 PPM and will be maintained automatically to a level of 3,500 PPM (minimum) to 7,000 PPM (maximum) for the duration of the treatment process. The ozone level is continuously monitored by an ozone sampling/monitoring unit, which is connected to the primary treatment chamber by, for example, a stainless-steel piping network. Connection to the primary treatment chamber is a preferred connection however the ozone sampling unit can be physically switched to the shredder screen area as require confirming the level of ozone present during the shredding phase of the process.

The primary treatment chamber is fitted with one or more agitators, specialized stirring mechanisms, to ensure high porosity of the incoming waste and full exposure to the ozone agent. Ozone is injected into the primary treatment chamber via multiple stainless-steel piping of flexible ozone lines. The ozone is injected into the top (highest point) of the primary treatment chamber. Ozone is 1.66 times heavier than air and will naturally settle and collect at the lowest point of the treatment chamber. The ozone level at this location (bottom of the bin) can be significantly higher than the level indicated by the ozone monitoring drawing samples from the top of the chamber. The agitator stirs the waste to enhance surface area exposure of the waste to the ozone and will reduce the delta variation in ozone levels in the chamber and eliminate this disparity once waste is added to the chamber.

The primary treatment chamber is fitted with a pressure equalization piping network to eliminate the possibility of pressure build up in the chamber by the injected ozone gas. This feature reduces the stress on shaft seals and the physical structure of the processing bin assembly. Any displaced gas from the bin is fed through the custom ozone destruct unit supplied with the treatment chamber. This custom ozone destruct unit can be installed on an ozone decanting chamber if the system is supplied with this optional bespoke feature. The ozone decanting chamber is built from high grade steel and is self-unloading. This allows our exemplary processing technology to operate on a continuous basis. The system is designed and built to operate twenty-four (24) hours per day and seven (7) days per week, as long as solid waste feed is available for treatment.

Prior art systems use low grade ozone created from air, whereas the present invention exemplary ozone technology uses only high-grade ozone produced from high grade oxygen produced on site from clean dry compressed air. The high-grade ozone is injected into the process at low pressure. Using a concentration of high-grade ozone requires less volumes of gas at low pressure to flow through the process to achieve the desired concentrations (PPM) for proper waste treatment. This practice reduces the risk of leakage or escape of ozone into the environment. Due to the higher quality of the ozone, less is more when it comes to the volume of applied ozone gas (sterilizing agent).

In some preferred embodiments, the primary treatment chamber is fitted with one-way air inlet valves to allow the exhaust fan ozone destruct unit to operate with little restriction. Fresh clean ambient air is allowed to enter the treatment chamber through the one-way air inlet valves to improve the dilution of the ozone in the treatment bin prior to unloading. Once the dwell time for the last amount of waste moved into the treatment chamber has expired, the ozone level is reduced to zero (0) making it safe to unload the treatment chamber. For system equipped with a decanting chamber, reducing the ozone level in the treatment chamber is not required prior to unloading. The ozone is reduced to zero in the decanting chamber as compared to in the primary treatment chamber. This allows the system to operate continuously as compared to batch with a dwell time delay and ozone reduction lag before the waste process cycle can be continued.

In those present invention embodiments wherein a separate decanting chamber is used in lieu of an exhaust stack unit, the decanting chamber option includes a dedicated Teledyne 465 M (or equivalent) ozone sampling unit connected to the HMI computer control panel. This feature ensures that the ozone level in the decanting chamber remains at zero during the unload process. Thus, in these embodiments, the ozone destruct unit is installed in the decanting chamber as compared to the primary treatment chamber. The facility is processing waste on a batch basis and can process the entire quantity of waste for that location allowing for the short dwell time delay between cycles to empty the primary treatment chamber when full.

Whether the decanting is done on a unit attached to the primary treatment chamber or in a separate downstream decanter chamber, the treated waste can be loaded into a "roll on"/"roll off" bin or into jumbo bags, or other approved containers for sterilized medical waste, for subsequent use or disposal.

The treated medical waste makes ideal daily cover at a landfill site or can be sent (sold) to a WTE (waste to energy) facility as high grade "renewable" fuel with a calorific value of 36.4 MJ/kg or 14,400 BTU/lbs. as measured by Cardiff University in Wales. The treated waste can also be used in cement plants as an alternative to fossil fuel and is classified as "renewable".

The preferred structural layout of the present invention advanced ozone treatment systems and technology is modular. This unique feature allows the system to be configured to meet the customer needs with minimal civil engineering/construction work or modifications to the area in which the unit is or is to be installed. Additionally, servicing and maintaining the various chambers and other components may be performed on their own at different cycles or schedules, and significantly, any components that need replacement may be replaced in a modular fashion.

In the present invention systems, waste is processed to 6 log 10 reduction (99.9999%) and this level of processing is standard reduction of the present invention exemplary technology. With a few minor adjustments, the process can be set for 4 log 10 or any other level of sterilization required by the local regulating body, i.e., Department of Health, EPA, Ministry of Health or Ministry of Environment.

Biological testing of the present invention systems is used to confirm that the system processing benchmark is achieved (base at 4 log 10 or, e.g., 6 log 10 reduction in required environs), both during the commissioning stage and into the future operation of the technology at intervals set out by the administrative and governing authorities. Therefore, a local or regional or country protocol for testing is prepared and provided for each location and jurisdiction.

Our technology treats waste at room temperature without heat or combustion or dangerous chemicals. Our technology has zero emissions and is efficient and effective. Any residual ozone from the process is converted back to oxygen through a catalyst (i.e., Carulite) or the ozone will revert back to oxygen naturally in about 30 minutes under normal atmospheric conditions. Only oxygen is exhausted to the atmosphere.

The drawings that follow are exemplary and illustrative of the present invention and not intended to limit or restrict the invention:

FIG. 1 is a block diagram showing the present invention solid/medical waste treatment systems and methods, frame 11, broken down into the four general stages of the present invention methods and systems. Frame 13 shows stage one: pre-shredding; frame 15 shows stage two: shredding and initial treatment; frame 17 shows stage three: primary treatment; and frame 19 shows stage four: ozone removal by destruction.

Figure 2:
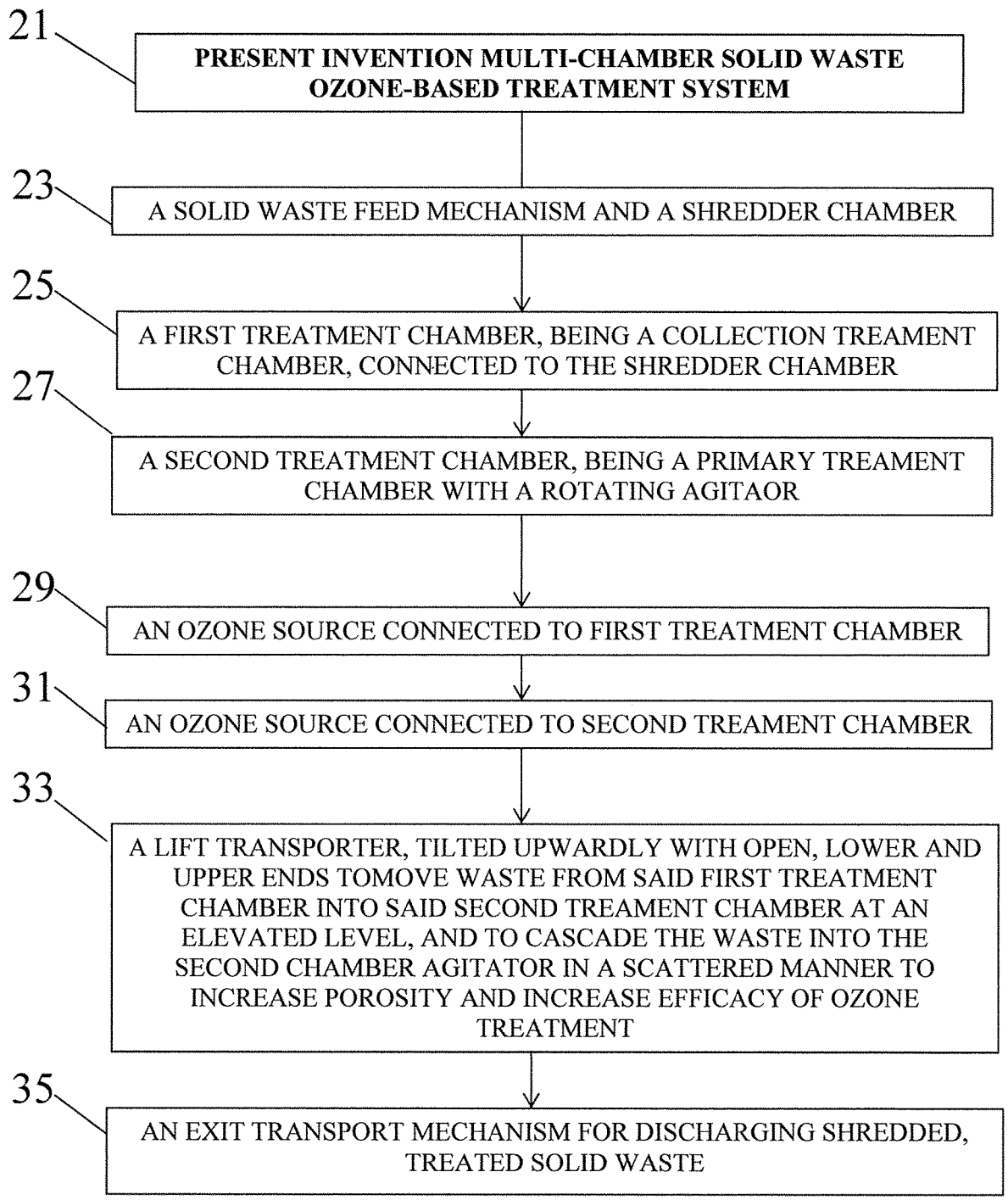
FIG. 2 shows another block diagram showing some additional features, details and options of the present invention methods and systems for treating medical waste and other solid waste materials.

FIG. 2 shows another block diagram, showing some additional features, details and options of the present invention methods and systems, frame 21, for treating medical waste and other solid waste materials. Frames 23, 25, 27, 29, 31, 33 and 35 illustrate the following components and descriptions, respectively: solid waste feed mechanism and shredder chamber, a first treatment chamber being a collection chamber, a second treatment chamber being a primary (high ozone density) treatment chamber with an agitator, an ozone source connected to the first chamber, an ozone source connected to the second chamber, a lift transporter for moving waste from the first to the second treatment chamber in a cascading fashion, and an exit transport mechanism.

Figure 3:
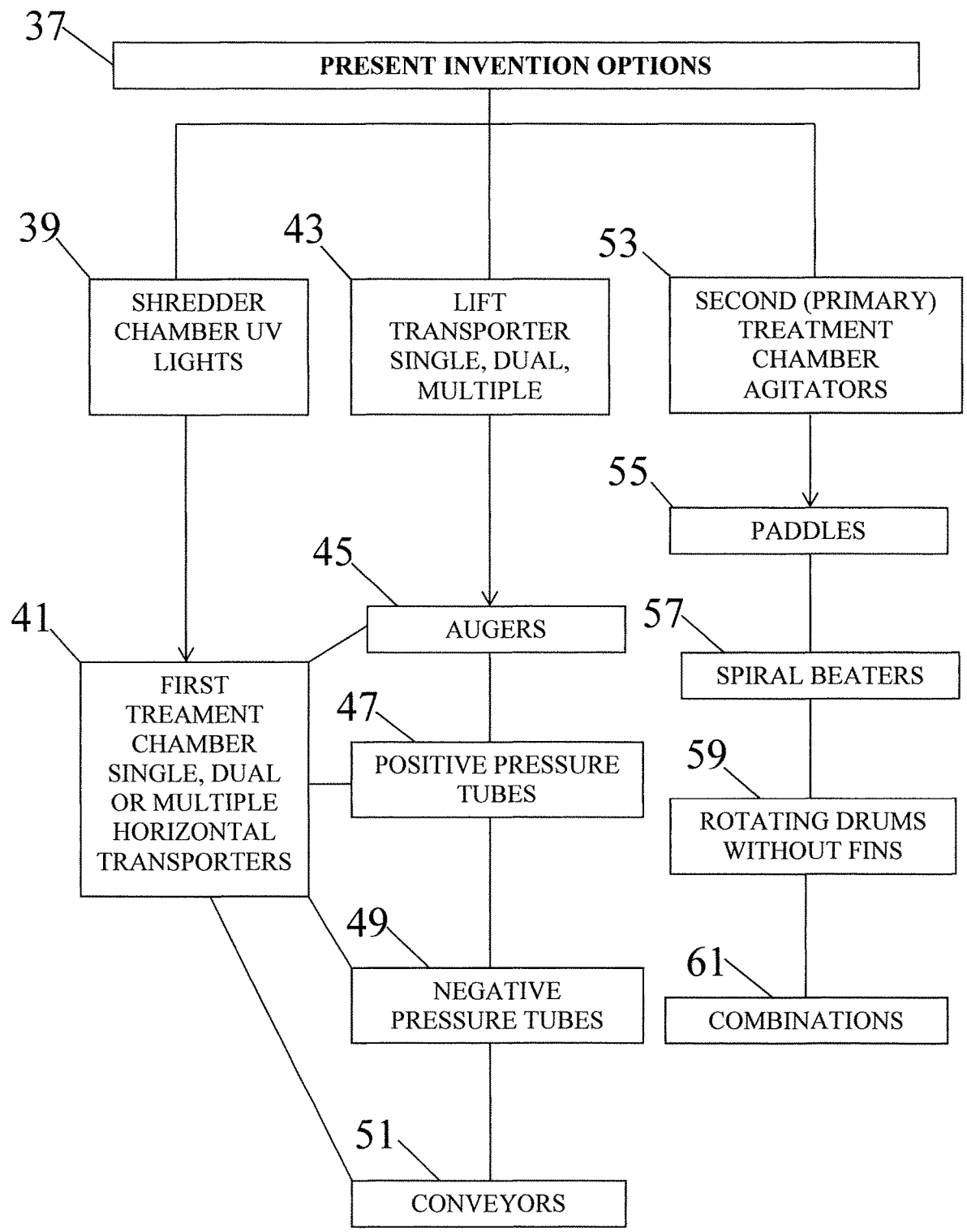
FIG. 3 shows another block diagram showing some additional options of the present invention methods and systems for treating medical waste and other solid waste materials.

FIG. 3 shows another block diagram showing some additional present invention options, frame 37, of the present invention methods and systems for treating medical waste and other solid waste materials. Frame 39 shows UV lights as described above; frame 41 shows first treatment chamber with single, dual, or multiple horizontal transporters, that may be, frame 45, augers; frame 47, positive pressure tubes; frame 49, negative pressure tubes; frame 51, conveyors. These same options for horizontal transporters are also options for single, double or multiple lift transporters, frame 43. The second (primary—high density ozone) treatment chamber agitators, frame 53, may be paddles, frame 55, beaters, frame 57; rotating drums with or without fins, frame 59 and combinations thereof, frame 61.

Figure 4:
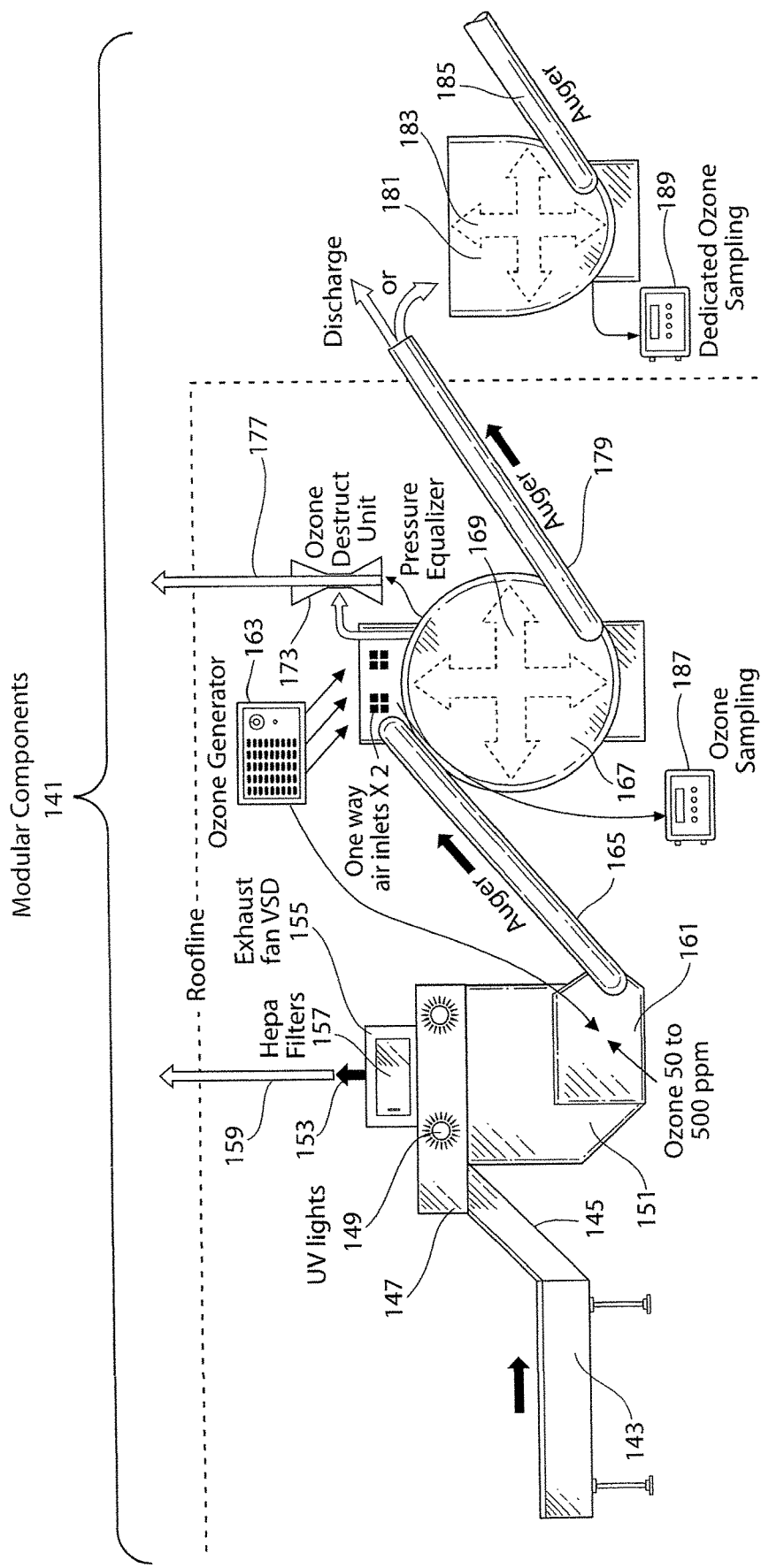
FIG. 4 is a front, diagrammatic view of one preferred embodiment of a present invention continuous, modular system for treating medical waste and other solid waste materials includes an optional ozone decanter unit chamber.
Figure 6:
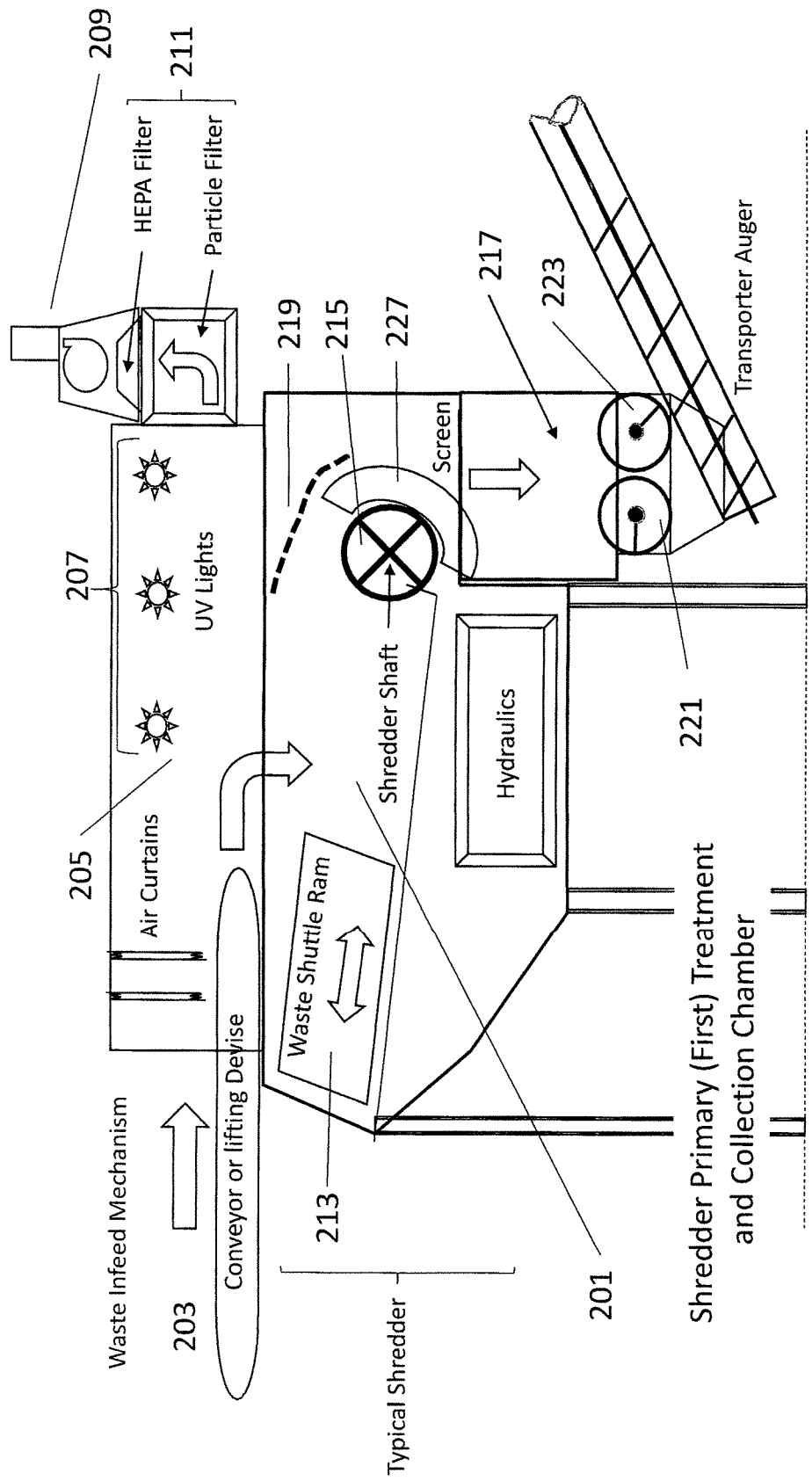
FIG. 6 shows a front cut view of details of a preferred embodiment shredder chamber and a first (collection) treatment chamber for a present invention system for treating medical waste and other solid waste materials.

FIG. 4 is a front, diagrammatic view of one preferred embodiment of a present invention continuous, modular system 141, for treating medical waste and other solid waste materials includes an optional ozone decanter unit chamber. This includes and infeed conveyor or tipping mechanism 143 and uptake conveyor 145, that moves untreated medical and other solid waste up and into hopper 147, with UV lights 149, and into shredder chamber 151. (Shredder chamber 151 would have detailed internal aspects such as is shown in FIG. 6 below.) There is a stack 153 atop shredder chamber 151, with a fan 155 and a set of Hepa filters 157 that emits clean air 159. Shredded waste from shredder chamber 151 is fed to initial treatment chamber 161, that contains a set concentration of ozone from ozone generator 163. Horizontal transporter(s) within chamber 161, (not shown, but see descriptions below), move the shredded, initially treated waste from chamber 161, to one or more lift transporter(s), such as auger 165. Auger 165 tumbles and drives the shredded waste out so as to cascade the waste into the second(primary) treatment chamber 167, with agitator 169. This chamber 167 also receives ozone, but at a higher concentration thar the first treatment chamber 151. As the waste is cascaded in to chamber 167 and subsequently agitated, the surface area exposure of the individual shredded waste pieces is enhanced two-fold. Thus, the porosity for enhanced ozone contact occurs from the cascading and again from the agitating. This significantly improves ozone treatment efficacy.

Next, remaining in FIG. 4, note that there are one way air inlets 171 that are controlled to balance the pressure within the treatment chamber 167. There is also an exhaust stack 175 with an ozone destruct unit 173 for clean exhaust 177. The detoxed, treated, clean waste is discharged via auger 179 or sent to an optional decanter chamber 181 with agitator 183 with subsequent discharge via auger 185 or via other equivalent discharge mechanism. When this optional decanter chamber 181 is used, then the destruct unit 173 may be eliminated. Ozone sampling may be monitored for the various chambers with ozone sampling unit 187 and, optionally, unit 189.

Figure 5:
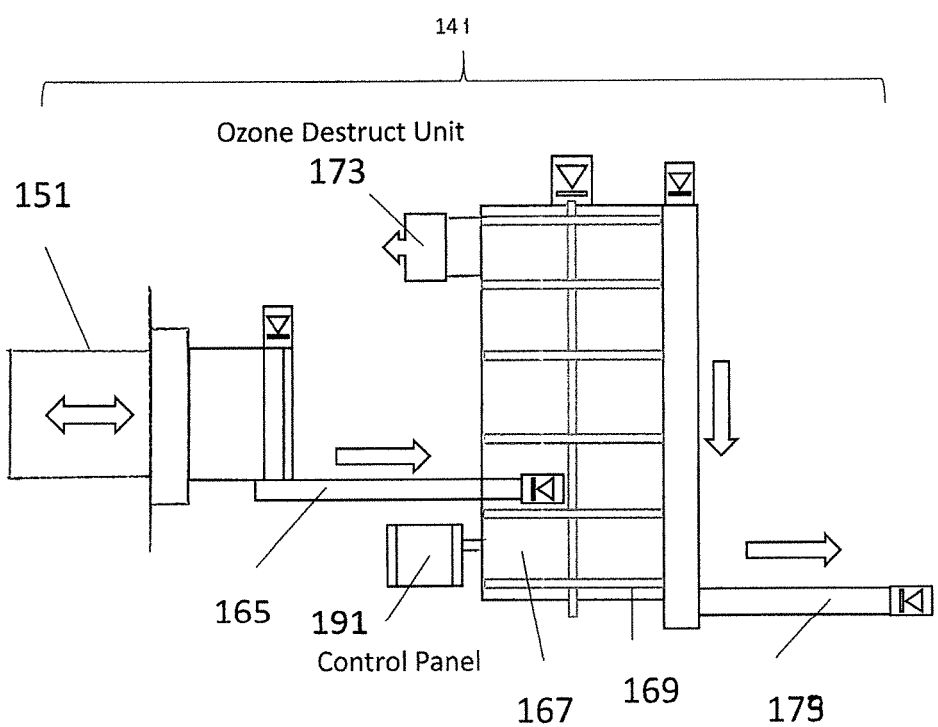
FIG. 5 shows a partial top view of the preferred embodiment of a present invention continuous, modular system for treating medical waste and other solid waste materials shown in FIG. 4.

FIG. 5 shows a partial top view of the preferred embodiment of a present invention continuous, modular system 141 for treating medical waste and other solid waste materials shown in FIG. 4. Identical parts are identically numbered and are therefore, not individually repeated or described here. Control panel 191 connects to various components and is used to set or program those components and functions, their flow rates, pressures, and ozone concentrations, as described elsewhere herein.

FIG. 6 shows a front cut view of details of a preferred embodiment shredder chamber 201 and a first (collection) treatment chamber 207 for a present invention system for treating medical waste and other solid waste materials. Here untreated waste is delivered via infeed 203 into hopper 205, which has UV lights 207 for initial bacteria, germs and other pathogen destruction. The hopper 205 has an exhaust stack 209 with a fan (not shown) and filters 211. The untreated waste drops into shredder chamber 201 and is pushed via ram 213 into shredder 215 with shroud 219. The shredded waste material, when it is sufficiently reduced, passes through screen 227 and int the low-density ozone first treatment chamber 217. Here, the shredded waste is exposed to low level ozone and is moved horizontally across the chamber 217 via dual horizontal transporter 221 and 223 to dual lift transporters such as auger 225.

Figure 7:
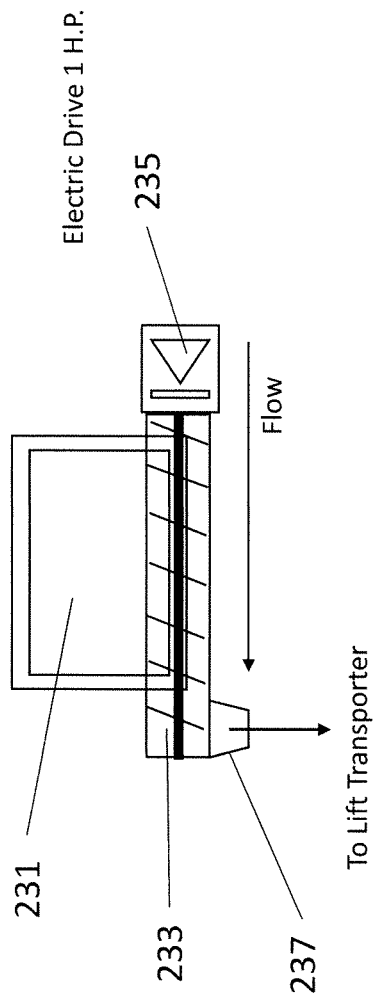
FIG. 7 shows a side view of another embodiment of a present invention component for continuous, modular system for treating medical waste and other solid waste, that component being a single horizontal auger for moving shredded waste to the lift transporter for subsequent cascading into the second (primary) treatment chamber.

FIG. 7 shows a side view of another embodiment of a present invention component for continuous, modular system for treating medical waste and other solid waste, that component being a single horizontal auger 233 in the base of another first collection treatment chamber 231 for moving shredded waste to the lift transporter via outlet 237 for subsequent cascading into the second (primary) treatment chamber. In this embodiment, the auger 233 is a single horizontal transporter for smaller systems and is driven by a 1 horsepower electric drive motor 235, as shown.

Figure 8:
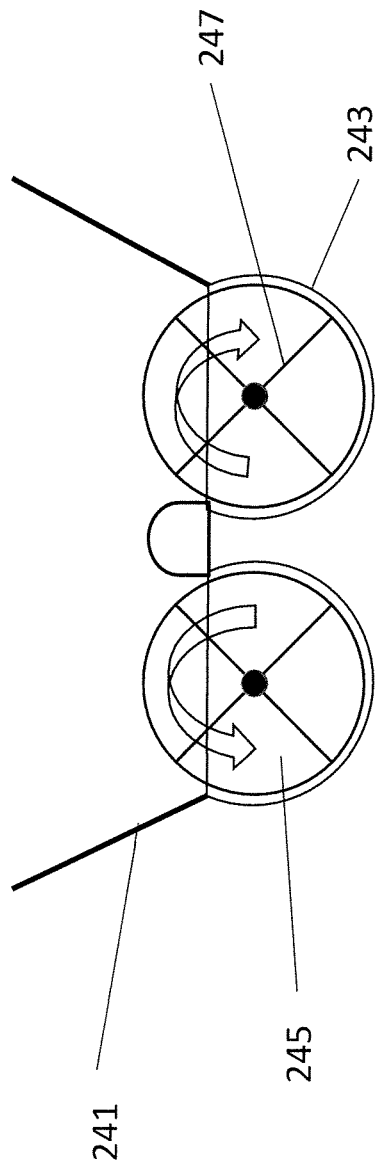
FIG. 8 shows a side view of another embodiment of a present invention component for continuous, modular system for treating medical waste and other solid waste, that component being dual horizontal augers for moving shredded waste inside the to the lift transporter for subsequent cascading into the second (primary) treatment chamber.
Figure 9:
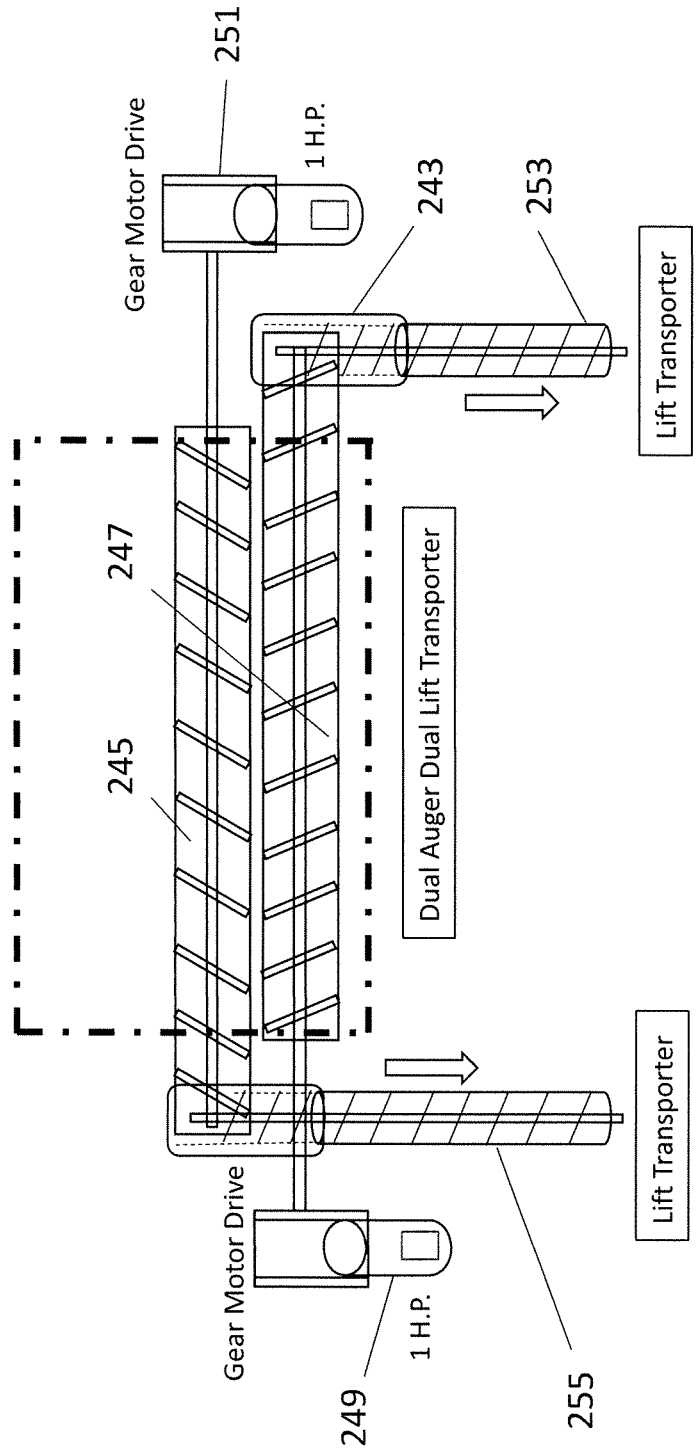
FIG. 9 shows a top rotated view thereof

FIG. 8 shows a side view of another embodiment of a present invention component for continuous, modular system for treating medical waste and other solid waste, that component being dual horizontal augers for moving shredded waste inside the to the lift transporter for subsequent cascading into the second (primary) treatment chamber, and FIG. 9 shows a top rotated view thereof In FIG. 8, there is a chamber with tapered sidewalls 241, auger saddle 243 and dual augers 245 and 247. These are used in larger systems with significantly greater volumetric flow. FIG. 9 shows the top view thereof with identical parts identically numbered. Also shown in FIG. 9 are drive motors 249 and 251 and outlets 253 and 255 to dual lift transporters.

Figure 10:
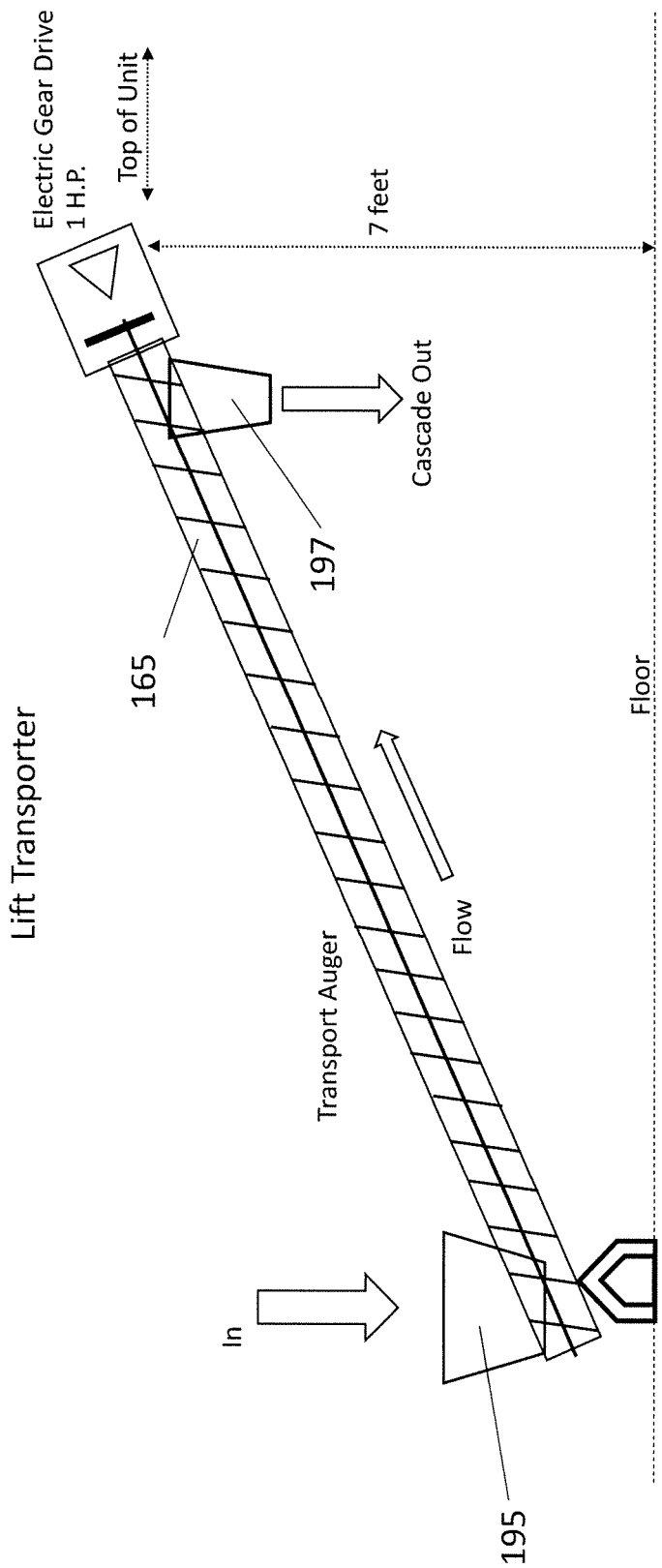
FIG. 10 shows a side view of a present invention preferred lift transporter for moving shredded, initially treated waste from the first treatment chamber to the second treatment chamber, which may be a stand-alone or one of a dual set of lift transporter augers.

FIG. 10 shows a side view of a present invention preferred lift transporter 165 for moving shredded, initially treated waste from the first treatment chamber to the second treatment chamber in a cascading fashion, which may be a stand-alone or one of a dual set of lift transporter augers. Auger 165 (from FIGS. 4 and 5, above) has a lower, open end inlet 195 and an open, cascading, upper outlet 197 for freely cascading shredded waste to the second treatment chamber.

Figure 11:
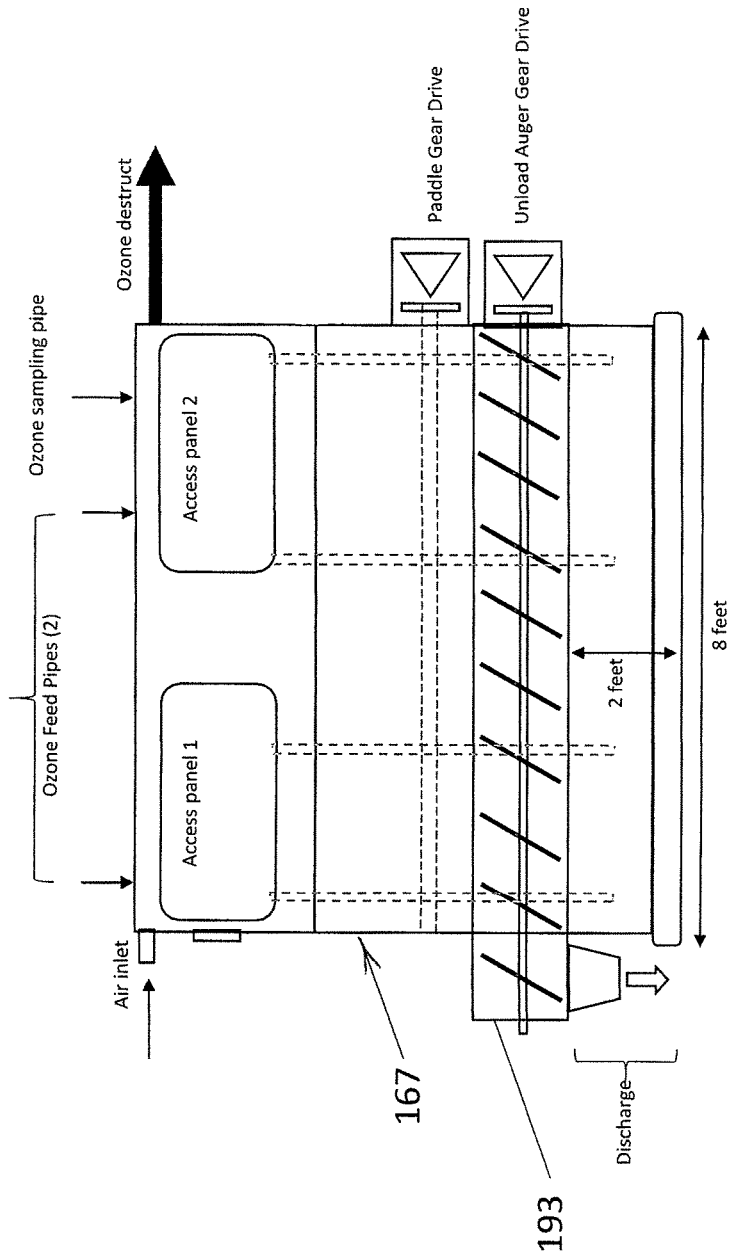
FIG. 11 shows a right side cut view of a present invention primary (second) treatment chamber shown in FIG. 4, FIG.
Figure 12:
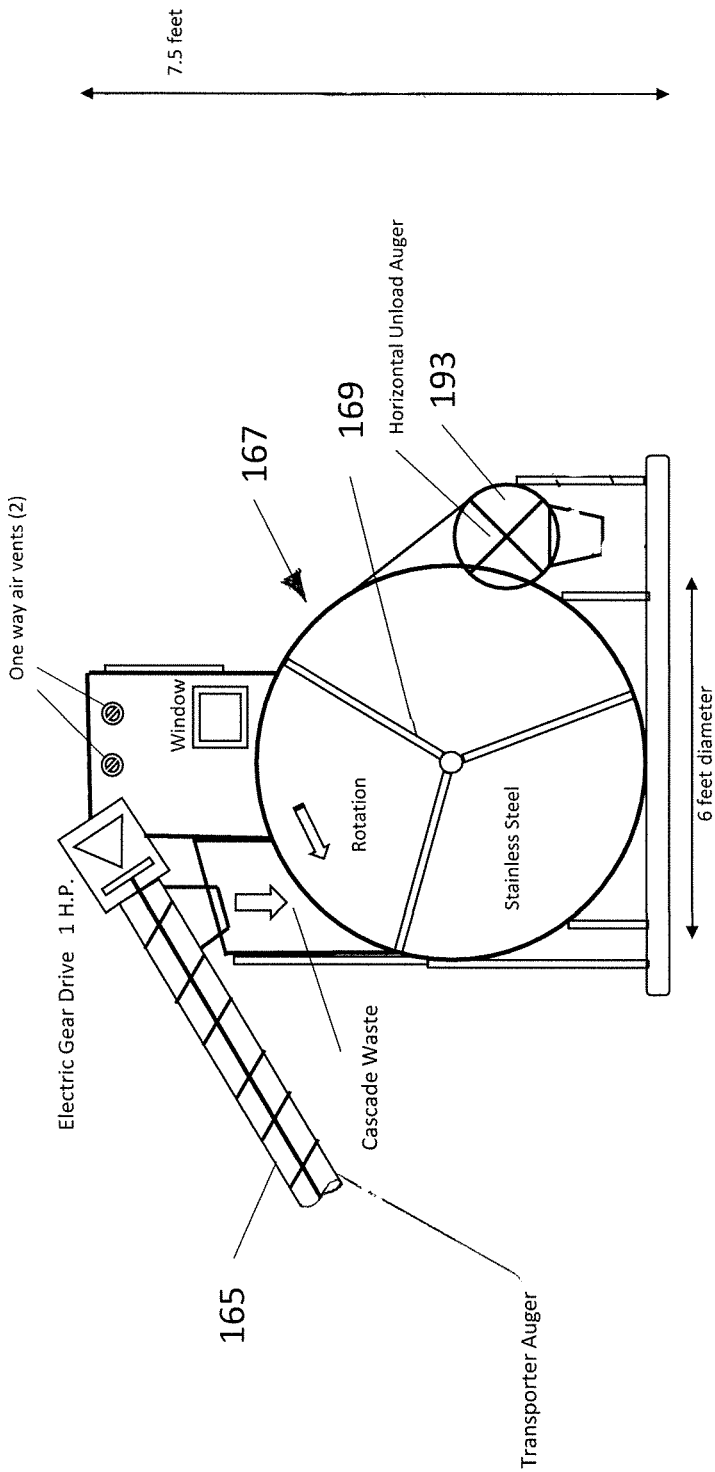
Figure 13:
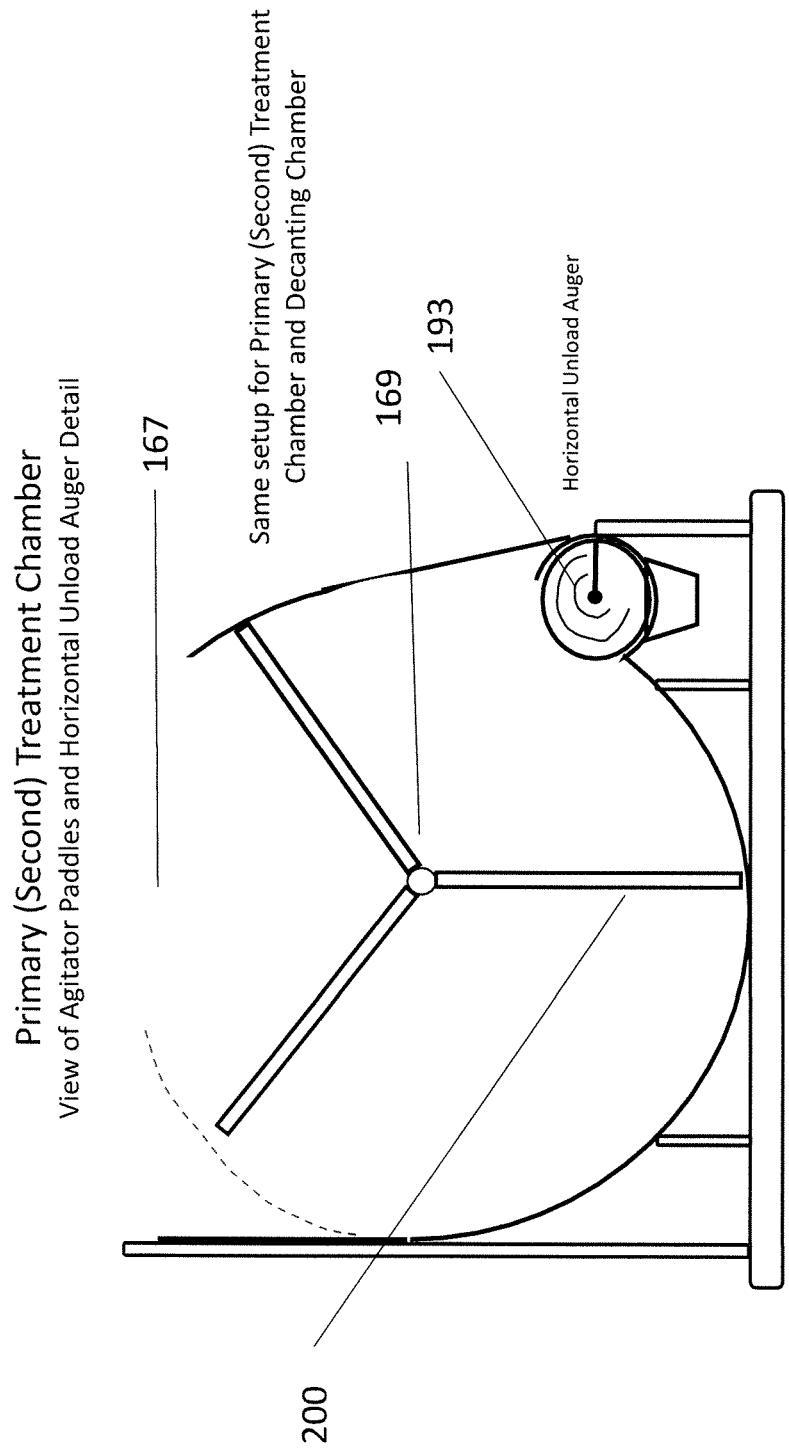
FIG. 13 shows a partial cut front view of a portion of a present invention primary (second) treatment chamber focused upon the agitator paddles and the discharge auger.

FIG. 11 shows a right side cut view of a present invention primary (second) treatment chamber 167, shown in FIG. 4, with details of discharge auger 193 shown, and FIG. 12 shows a front view thereof, with components from FIGS. 4 and 11 identically numbered. FIG. 13 shows a partial cut front view of a portion of a present invention primary (second) treatment chamber 167, described above, focused upon the agitator 169 and its paddles 200, and the discharge auger 193.

In summary, the present invention systems and methods have numerous new and superior features to prior art systems and offer environmentally favorable results with exceptional efficacy.

Although particular embodiments of the invention have been described in detail herein with reference to the accompanying drawings, it is to be understood that the invention is not limited to those particular embodiments, and that various changes and modifications may be affected therein by one skilled in the art without departing from the scope or spirit of the invention as defined in the appended claims. For example, the shapes of the various components herein may be changed; the components may have functionally equivalent substitutions, such as multiple agitators instead of one, or a drum rotating clockwise and a stationary set of paddles, without exceeding the scope of the present invention.

What is claimed is:

1. A multi-chamber solid waste ozone-based treatment system for treatment of solid waste that contains at least one pathogen, and requires apparent volume reduction, which comprises:
   a) a solid waste feed mechanism connected to a shredder chamber for feeding solid waste that contains at least one pathogen from a source into said shredder chamber;
   b) said shredder chamber having a shredder, said shredder adapted to shred and reduce apparent volume of said solid waste;
   c) a first treatment chamber, being a collection treatment chamber, functionally connected to said shredder chamber;
   d) a second treatment chamber, being a primary treatment chamber, said secondary chamber including at least one rotating agitator;
   e) at least one ozone source connected to said first treatment chamber for preliminary ozone molecular interaction with said solid waste to destroy at least a portion of said at least one pathogen;
   f) at least one ozone source connected to said second treatment chamber to inject ozone for ozone molecular interaction with said solid waste to destroy at least a portion of said at least one pathogen;
   g) at least one lift transporter, tilted upwardly to have an open, lower end and an open, upper end, said upper end being positioned within said second treatment chamber, and said lower end being functionally connected to said first treatment chamber to receive and move said solid waste from said first treatment chamber into said second treatment chamber at an elevated level, and to cascade said solid waste out of said at least one lift transporter and into said second chamber in a scattered manner to increase surface area exposure of said solid waste to said ozone to increase efficacy of ozone treatment, said at least one lift transporter open upper end being positioned to also feed said solid waste into said at least one agitator for further scattering of said solid waste to further increase surface area exposure of said solid waste to said ozone to further increase efficacy of ozone treatment; and
   h) an exit transport mechanism for discharging shredded, treated solid waste from said second treatment chamber and into a transport device for disposal;
   wherein said at least one ozone source connected to said first treatment chamber is adapted to provide ozone at 50 to 500 ppm and said at least one ozone source connected to said second treatment chamber is adapted to provide ozone at 5000 to 7000 ppm.

2. The multi-chamber solid waste ozone-based treatment system of claim 1 wherein said at least one lift transporter is a plurality of lift transporters.

3. The multi-chamber solid waste ozone-based treatment system of claim 1 wherein said at least one lift transporter is selected from the group consisting of a positive pressure transporter, a negative pressure transporter, a conveyor transporter, and an auger transporter.

4. The multi-chamber solid waste ozone-based treatment system of claim 3 wherein said at least one lift transporter is an auger transporter.

5. The multi-chamber solid waste ozone-based treatment system of claim 1 wherein said at least one agitator is selected from the group consisting of rotating paddles, rotating spiral fins, rotating drum, and rotating drum with fins.

6. The multi-chamber solid waste ozone-based treatment system of claim 1 wherein said shredder chamber, said first treatment chamber and said second treatment chamber are separate modular units.

7. A multi-chamber solid waste ozone-based treatment system for treatment of solid waste that contains at least one pathogen, and requires apparent volume reduction, which comprises:
   a) a solid waste feed mechanism connected to a shredder chamber for feeding solid waste that contains at least one pathogen from a source into said shredder chamber;
   b) said shredder chamber having a shredder, said shredder adapted to shred and reduce apparent volume of said solid waste;
   c) a first treatment chamber, being a collection treatment chamber, functionally connected to said shredder chamber;
   d) a second treatment chamber, being a primary treatment chamber, said secondary chamber including at least one rotating agitator;
   e) at least one ozone source connected to said first treatment chamber for preliminary ozone molecular interaction with said solid waste to destroy at least a portion of said at least one pathogen;
   f) at least one ozone source connected to said second treatment chamber to inject ozone for ozone molecular interaction with said solid waste to destroy at least a portion of said at least one pathogen;
   g) at least one lift transporter, tilted upwardly to have an open, lower end and an open, upper end, said upper end being positioned within said second treatment chamber, and said lower end being functionally connected to said first treatment chamber to receive and move said solid waste from said first treatment chamber into said second treatment chamber at an elevated level, and to cascade said solid waste out of said at least one lift transporter and into said second chamber in a scattered manner to increase surface area exposure of said solid waste to said ozone to increase efficacy of ozone treatment, said at least one lift transporter open upper end being positioned to also feed said solid waste into said at least one agitator for further scattering of said solid waste to further increase surface area exposure of said solid waste to said ozone to further increase efficacy of ozone treatment;
   h) an exit transport mechanism for discharging shredded, treated solid waste from said second treatment chamber and into a transport device for disposal; and,
   i) an ozone destruction device functionally connected to said system downstream from said second treatment chamber to prevent ozone release from said system to the atmosphere.

8. The multi-chamber solid waste ozone-based treatment system of claim 7 wherein said ozone destruction device is positioned in an exhaust above said second treatment chamber.

9. The multi-chamber solid waste ozone-based treatment system of claim 7 wherein there is a decanting chamber functionally connected to said second treatment chamber and positioned between said second treatment chamber and said exit transport mechanism, said ozone destruction device is connected to said decanting chamber.

10. The multi-chamber solid waste ozone-based treatment system of claim 9 wherein said decanting chamber includes at least one rotating agitator.

11. The multi-chamber solid waste ozone-based treatment system of claim 10 wherein said at least one agitator in said decanting chamber is selected from the group consisting of rotating paddles, rotating spiral fins, rotating drum, and rotating drum with fins.

12. An ozone-based method for treatment of solid waste that contains at least one pathogen, and requires apparent volume reduction, which comprises:
   a) feeding solid waste that contains at least one pathogen from a source into a shredder chamber with a shredder;
   b) shredding said solid waste to reduce apparent volume of said solid waste;
   c) feeding said solid waste from said shredder chamber to a first treatment chamber having an ozone source connected thereto, being a collection treatment chamber, for preliminary ozone molecular interaction with said solid waste to destroy at least a portion of said at least one pathogen;
   d) feeding said solid waste from said first treatment chamber to a second treatment chamber having an ozone source connected thereto, via at least one lift transporter, tilted upwardly and having an open, lower inlet end and an open, upper outlet end, so as to cascade the solid waste out of said at least one lift transporter and into said second chamber in a scattered manner to increase surface area exposure of said solid waste to said ozone, and to increase efficacy of ozone treatment; said second treatment chamber being a primary treatment chamber, said second treatment chamber including at least one rotating agitator; and said second treatment chamber being connected to an ozone decanting unit with an ozone pressure equalization subsystem;
   e) agitating said solid waste that has been cascaded, with a rotating agitator located in said second treatment chamber for further scattering of said solid waste to further increase surface area exposure of said solid waste to said ozone and to further increase efficacy of ozone treatment; at least one said first treatment chamber;
   f) eliminating remaining ozone from said solid waste via said ozone decanting unit with said ozone pressure equalization subsystem; and,
   g) discharging the shredded, treated solid waste with an exit transport mechanism into a transport device for disposal;
wherein said ozone source connected to said first treatment chamber is adapted to provide ozone at 50 to 500 ppm and said ozone source connected to said second treatment chamber is adapted to provide ozone at 5000 to 7000 ppm.

13. The ozone-based method for treatment of solid waste of claim 12 wherein said at least one lift transporter is a plurality of lift transporters.

14. The ozone-based method for treatment of solid waste of claim 12 wherein said at least one lift transporter is selected from the group consisting of a positive pressure transporter, a negative pressure transporter, a conveyor transporter, and an auger transporter.

15. The ozone-based method for treatment of solid waste of claim 14 wherein said at least one lift transporter is an auger transporter.

16. The ozone-based method for treatment of solid waste of claim 12 wherein said at least one agitator is selected from the group consisting of rotating paddles, rotating spiral fins, rotating drum, and rotating drum with fins.

17. The ozone-based method for treatment of solid waste of claim 12 wherein said method further comprises eliminating unspent ozone in an ozone destruction device functionally connected downstream from said second treatment chamber to prevent ozone release to the atmosphere.

18. The ozone-based method for treatment of solid waste of claim 17 wherein said ozone destruction device is positioned in an exhaust above said second treatment chamber.

19. The ozone-based method for treatment of solid waste of claim 12 wherein there is a decanting chamber functionally connected to said second treatment chamber and positioned between said second treatment chamber and said exit transport mechanism, said ozone destruction device is connected to said decanting chamber.

20. The ozone-based method for treatment of solid waste of claim 19 wherein said decanting chamber includes at least one rotating agitator.

21. The ozone-based method for treatment of solid waste of claim 20 wherein said at least one agitator in said decanting chamber is selected from the group consisting of rotating paddles, rotating spiral fins, rotating drum, and rotating drum with fins.

22. The ozone-based method for treatment of solid waste of claim 12 which further includes treating said solid waste with ultraviolet light prior to shredding.

23. The ozone-based method for treatment of solid waste of claim 12 wherein said method is a continuous process.

* * * * *